(12) United States Patent
Koob et al.

(10) Patent No.: US 8,420,377 B2
(45) Date of Patent: Apr. 16, 2013

(54) TRANSGENOMIC MITOCHONDRIA, TRANSMITOCHONDRIAL CELLS AND ORGANISMS, AND METHODS OF MAKING AND USING

(75) Inventors: Michael D. Koob, Roseville, MN (US); Young G. Yoon, Cottage Grove, MN (US)

(73) Assignees: Michael D. Koob, Roseville, MN (US); Young G. Yoon, Cottage Grove, MN (US)

( * ) Notice: Subject to any disclaimer, the term of this patent is extended or adjusted under 35 U.S.C. 154(b) by 804 days.

(21) Appl. No.: 11/578,476

(22) PCT Filed: Apr. 15, 2005

(86) PCT No.: PCT/US2005/012872
§ 371 (c)(1),
(2), (4) Date: Oct. 13, 2006

(87) PCT Pub. No.: WO2005/103229
PCT Pub. Date: Nov. 3, 2005

(65) Prior Publication Data
US 2009/0098653 A1    Apr. 16, 2009

Related U.S. Application Data

(60) Provisional application No. 60/562,642, filed on Apr. 15, 2004.

(51) Int. Cl.
*C12N 1/19* (2006.01)
*C12N 15/85* (2006.01)

(52) U.S. Cl.
USPC ...................................... 435/254.2; 435/455

(58) Field of Classification Search ........................ None
See application file for complete search history.

(56) References Cited

PUBLICATIONS

Johnston et al. Science Jun. 10, 1988. vol. 240. pp. 1538-1541.*
Barrientos and Moraes (Human Molecular Genetics, 1998. vol. 7, No. 11, pp. 1801-1808).*
Mckenzie et al.(PNAS, 2004, vol. 101, No. 6, pp. 1685-1690).*
Legros et al (Molecular Biology of the Cell, 2002. vol. 13, pp. 4343-4354).*
Foury (The Journal of Biological Chemistry, 1989. vol. 264, No. 34, pp. 20552-20560).*
Yoon et al. Anatomy and Cell Biology, 2010, vol. 43, pp. 97-109.*
Yoon and Koob, Journal of Genetics and Genomics, 2011, vol. 38, pp. 173-179.*
Fox et al (PNAS, 1988. vol. 85, pp. 7288-7292).*
Giordano, C. et al. Pathogenesis of the Deafness-Associated A1555G Mitochondrial DNA Mutation. Biochemical and Biophysical Research Communications. 2002. vol. 293 pp. 521-529.
Pinkert, C. et al. Production of Transmitochondrial Mice. Method. 2002. vol. 26. pp. 348-357.
Yoon, Y. G. et al. Efficient cloning and engineering of entire mitochondrial genomes in *Escherichia coli* and, etc. Nucleic Acids Research. 2003. vol. 31 No. 5. pp. 1407-1415.
Dimauro, S. et al. Mitochondrial DNA Mutations in Human Disease. American Journal of Medical Genetics. 2001. vol. 106. pp. 18-26.
Dahl, H.-H.M. et al. Mitochondrial Diseases: Beyond the Magic Circle. American Journal of Medical Genetics. 2001. vol. 106. pp. 1-3.
Williams, A. J. et al. A Novel System for Assigning the Mode of Inheritance in Mitochondrial Disorders Using, etc. Human Molecular Genetics. 1999. vol. 8 No. 9. pp. 1691-1697.

\* cited by examiner

*Primary Examiner* — Celine Qian
(74) *Attorney, Agent, or Firm* — Hemingway & Hansen, LLP; D. Scott Hemingway

(57) ABSTRACT

The invention provides transgenomic mitochondria, transmitochondrial cells and organisms, and the materials and methods for making such mitochondria, cells, and organisms.

4 Claims, 7 Drawing Sheets

TRANSGENOMIC MITOCHONDRIA, TRANSMITOCHONDRIAL CELLS AND ORGANISMS, AND METHODS OF MAKING AND USING

CROSS-REFERENCE TO RELATED APPLICATIONS

This application is the national stage of international application no. PCT/US2005/012872, filed 15 Apr. 2005, which claims the benefit of provisional application No. 60/562,642 filed 15 Apr. 2004

TECHNICAL FIELD

This invention generally relates to mitochondria and mitochondrial DNA, and more particularly to transgenomic mitochondria and transmitochondrial cells and organisms.

BACKGROUND

The mammalian mitochondrial genome is a small, circular, double-stranded molecule containing 37 genes. Of these, 24 (22 tRNAs and two rRNAs) are needed for mitochondrial DNA translation, and 13 encode subunits of the respiratory chain complexes. Many mitochondrial processes are strictly dependent on the interaction between specific mitochondrial DNA sequences and the nuclear-encoded mitochondrial polypeptides with which they have co-evolved. Therefore, the majority of mitochondrial polypeptides are nuclear encoded, translated in the cytoplasm, and then transported across one or both of the mitochondrial membranes. It is thought that mitochondria contain more than 1,000 different proteins.

SUMMARY

The invention discloses methods of transferring isolated mitochondrial genomes into purified mitochondria or into mitochondria within a cell. Mitochondria containing exogenous mitochondrial genomes are "transgenomic mitochondria," while cells or organisms containing exogenous mitochondrial genomes in the mitochondria are "transmitochondrial cells" or "transmitochondrial organisms." The invention provides such transgenomic mitochondria and transmitochondrial cells and organisms.

Using the methods of the invention, a mitochondrial genome can be manipulated prior to introducing it into mitochondria. In addition, basic mitochondria-specific processes can be transferred into transmitochondrial cells by introducing the appropriate nuclear genes into the transmitochondrial cells. In one aspect, the invention provides a transmitochondrial cell including an isolated exogenous mitochondrial genome. Representative cells can include yeast cells, mammalian cells, avian cells, bovine cells, and porcine cells. Representative exogenous mitochondrial genomes include mouse mitochondrial genomes and human mitochondrial genomes.

In another aspect, the invention provides for a transmitochondrial yeast cell that includes a transcriptionally active mammalian mitochondrial genome. A representative mammalian mitochondrial genome is a mouse mitochondrial genome. In still another aspect, the invention provides a transmitochondrial yeast cell that includes a yeast mitochondrion that is substantially free of yeast mitochondrial DNA and that includes an isolated mammalian mitochondrial genome. Such a transmitochondrial yeast cell also can include an exogenous nuclear gene from the same species as the mitochondrial genome. The exogenous nuclear gene can encode, for example, a mitochondrial transcription factor or a polypeptide involved in replication of the mitochondrial genome. In yet another aspect, the invention provides a transgenomic yeast mitochondrion that includes a mammalian mitochondrial genome. Representative mammalian mitochondrial genomes include mouse mitochondrial genomes and human mitochondrial genomes. In one embodiment, the mitochondrion is substantially free of endogenous mitochondrial DNA.

The invention also provides for a transmitochondrial mammalian cell that contains such a transgenomic yeast mitochondrion. In another aspect, the invention provides a transgenomic mitochondrion that includes an exogenous mitochondrial genome. A representative transgenomic mitochondrion is a human mitochondrion. In still another aspect, the invention provides for a vector that includes a mammalian mitochondria genome and a prokaryotic low-copy number origin of replication. Such a vector also can include a prokaryotic selectable marker or a prokaryotic screening marker, and/or an eukaryotic selectable marker or an eukaryotic screening marker.

In yet another aspect, the invention provides a mammalian mitochondria genome that includes a prokaryotic low-copy number origin of replication. Such a genome also can include a prokaryotic selectable marker or a prokaryotic screening marker, and/or an eukaryotic selectable marker or an eukaryotic screening marker. In one aspect, the invention provides a method for introducing an isolated mammalian mitochondrial genome into a yeast mitochondrion. Such a method includes providing a yeast cell that includes mitochondria that are substantially free of endogenous DNA; and introducing isolated mammalian mitochondrial genomes into the mitochrondria. In an embodiment of the invention, the mammalian mitochondrial genomes are introduced into the yeast mitochondria by particle bombardment. In one aspect, the invention provides a method for introducing an isolated exogenous mammalian mitochondrial genome into a mammalian mitochondrion. Such a method includes providing a mammalian cell that includes mitochondria that are substantially free of endogenous DNA; and introducing the exogenous isolated mammalian mitochondrial genomes into the mitochrondria.

In an embodiment of the invention, the exogenous isolated mammalian mitochondrial genomes are introduced into the mitochondria by particle bombardment. In another aspect, the invention provides a method for introducing an isolated exogenous mammalian mitochondrial genome into a mammalian mitochondrion. Such a method includes providing purified transgenomic yeast mitochondria that contains an isolated mammalian mitochondrial genome; injecting the purified transgenomic yeast mitochondria into mammalian cells having mammalian mitochondria. In still another aspect, the invention provides a transmitochondrial mammal that has mitochondria containing exogenous isolated mammalian mitochondrial genomes. Representative mammals can include mice, rats, or monkeys. In yet another aspect, the invention provides a transmitochondrial plant that has mitochondria containing exogenous isolated mitochondrial genomes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control. The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

FIG. 2A is a schematic of the approach used to clone fragments from the mouse mitochondrial genome with promoter activity. FIG. 2B is a comparison of CAT activities generated from mitochondrial DNA promoter fragments at low and high copy numbers. The black and gray bars shown for each clone indicate the relative CAT activities from low copy and high copy strains, respectively, with the value of the low copy vector-only control arbitrarily set to 1.

Like reference symbols in the various drawings indicate like elements.

DETAILED DESCRIPTION OF THE PREFERRED EMBODIMENTS

Figure 1:
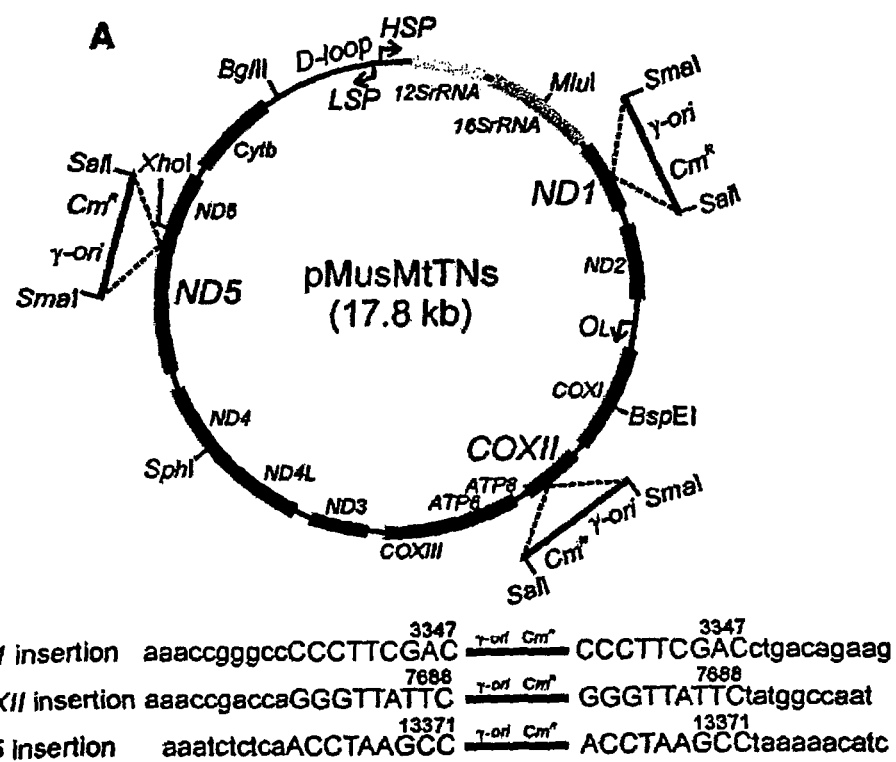
FIG. 1 is a schematic showing three mouse mitochondrial DNA clones generated by an in vitro transposition reaction.

Saccharomyces cerevisiae yeast strains were generated that contain entire mouse mitochondrial genomes in their mitochondria rather than their own yeast mitochondrial DNA. Any mitochondrial genome can be manipulated using routine recombinant techniques and propagated using standard prokaryotic strains. Therefore, a new in vivo mammalian mitochondrial model system has been created in which the mitochondrial sequences can be genetically engineered. By adding the appropriate mammalian genes for nuclear-encoded mitochondrial proteins to these yeast strains, such species-specific mitochondrial processes as transcription and replication are recapitulated in these transmitochondrial yeast strains. This methodology can be used to introduce any isolated exogenous mitochondrial genomes into the mitochondria of any eukaryotic cell.

Mitochondria, Mitochondrial DNA, and Eukaryotic Cells

The present invention provides transgenomic mitochondria and transmitochondrial cells and organisms. Transgenomic mitochondria can be generated by introducing isolated exogenous mitochondrial genomes into purified mitochondria. Transmitochondrial cells and organisms can be generated by introducing isolated exogenous mitochondrial genomes into mitochondria within a cell, or by introducing transgenomic mitochondria into a cell or organism.

Mitochondria can be purified using any of a number of different gradient methods. (Sambrook et al., 1989, Molecular Cloning: A Laboratory Manual, 2nd Ed., Cold Spring Harbor Laboratory Press, Cold Spring Harbor, N.Y.; and Cavelier et al., 2000, Exp. Cell Res., 259: 79-85). Mitochondria useful in the invention are substantially free of DNA. As used herein, "substantially free" is intended to mean mitochondria that are nearly or completely void of DNA (i.e., mitochondrial DNA is present in the mitochondria in small amounts or is present in only a small number of mitochondria).

Mitochondrial DNA can be removed from mitochondria using a variety of methods. In yeast, cells lacking DNA in their mitochondria can be obtained by spontaneous mutation or by treatment with a DNA-targeting drug such as acriflavin. These yeast cells have been referred to as "petite mutants" because they are deficient in respiration and therefore, smaller in size than wild-type yeast cells. See, for example, Chen & Clark-Walker, 2000, Int. Rev. Cytol., 194: 197-238. Alternatively, cells can be treated with a DNA intercalator such as rhodamine 6G or ethidium bromide. When eukaryotic cells are exposed to a DNA intercalator, replication in the circular genomes of mitochondria is blocked, and the mitochondrial genomic DNA is eventually lost. See, for example, Williams et al., 1999, Human Mol. Genetics, 8: 1691-7 and Desjardins et al., 1985, Mol. Cell. Biol., 5: 1163-9.

As used herein, "exogenous" is generally defined as "originating or derived externally." "Externally" typically means from a different source. For example, mitochondrial genomes are exogenous to host cells or host mitochondria when the mitochondrial genomes originate from different cell types or different species than the host cells or host mitochondria. In addition, "exogenous" can also refer to mitochondrial genomes that are removed from mitochondria, manipulated, and returned to the same mitochondria. As used herein, "endogenous" is generally defined as "originating or derived internally." For example, endogenous mitochondria are mitochondria that are native to a cell.

A mitochondrial genome refers to the circular nucleic acid present in a mitochondrion. Mitochondrial genomes can be obtained from any number of organisms including mammalian organisms such as, without limitation, mice and humans. As used herein, mitochondrial "genome" refers to the complete mitochondrial genome (i.e., 100%) or at least 80% (e.g., at least 85%, 90%, 95%, or 99%) of a naturally occurring mitochondrial genome.

Generally, mitochondrial genomes are isolated so that the genomes can be manipulated in any number of ways prior to introduction into the mitochondria of the same or a different organism. Methods of isolating mitochondrial genomes are known in the art. See, for example, Hudson et al., 1969, PNAS USA, 62: 813-20; Ausenda & Chomyn, 1996, Methods Enzymol., 264: 122-128; and Beckman et al., 1993, Promega Notes Magazine, 43:10. As used herein, "isolated" refers to mitochondrial genomes that are separated from other nucleic acids usually associated with mitochondrial genomes in their natural state. In addition, isolated mitochondrial genomes can be genetically engineered, recombinant, and/or synthetic mitochondrial genomes. Mitochondrial genomes or fragments thereof existing among hundreds to millions of other nucleic acids within, for example, a nucleic acid library (e.g., a cDNA, or genomic library) or a portion of a gel (e.g., agarose, or polyacrylamine) containing restriction-digested DNA are not to be considered isolated mitochondrial genomes.

Isolated mitochondrial genomes can be obtained using isolation techniques routine in the art such as those exemplified herein. In addition, isolated mitochondrial genomes within the scope of the invention can be obtained using other methods including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995; and U.S. Pat. Nos. 4,683,202, 4,683,195, 4,800,159, and 4,965,188. Recombinant nucleic acid techniques include, for example, restriction enzyme digestion and ligation. Isolated nucleic acids of the invention also can be chemically synthesized, either as a single nucleic acid molecule or as a series of oligonucleotides. In addition, isolated nucleic acid molecules of the invention also can be obtained by mutagenesis.

Mitochondrial genomes can be, but do not necessarily need to be, cloned into a vector. Mitochondrial genome sequences can be produced and manipulated by recombinant DNA technology methods routine in the art. Sequences that allow mitochondrial genomes to be amendable to manipulation include, for example, origin of replication sequences and additional sequences such as those encoding a selectable marker (e.g., an antibiotic resistance gene) or a screenable marker (e.g., glucuronidase (GUS)).

An origin of replication sequence can include a prokaryotic origin of replication, which initiates replication of nucleic acid sequences in prokaryotes, or a eukaryotic origin of replication (also referred to as an "autonomously replicating sequence" (ARS)), which initiates replication of nucleic acid sequences in eukaryotes. Origin of replication sequences can be generally referred to as "low-copy number" origins and "high-copy number" origins based upon the number of rounds of replication initiated. Mitochondrial genomes are generally more stable with a low-copy number origin of replication (e.g., $\leqq 25$ copies of mitochondrial genomes/cell, e.g., 1 copy/cell, 5 copies/cell, 10 copies/cell, 15 copies/cell, 20 copies/cell, or 25 copies/cell).

Screenable and selectable markers are typically used to identify and separate, respectively, those cells containing nucleic acid encoding the marker from cells that don't contain the marker nucleic acid. Screenable markers generally produce a colored or fluorescent product when provided with the appropriate substrate and include but are not limited to glucuronidase (GUS), β-galactosidase (β-gal), luciferase, or green fluorescent protein (GFP). Selectable markers can provide resistance to a compound (e.g., an antibiotic or a herbicide) and include but are not limited to NPTII (encoding resistance to kanamycin), and HPT (encoding resistance to hygromycin).

TABLE 1

List of Selectable and Screenable Markers

| Type or Source of Marker | Enzyme/Mode of Action | Selection Agent/Substrate | Reference |
|---|---|---|---|
| A. Selectable markers I. Antibiotics | | | |
| Neomycin phosphotransferse II gene (neo) | Neomycin phosphotransferase type II (NPT II), detoxification | Neomycin/kanamycin antibiotic C418 | Bevan et al., 1983, Nature, 304: 184-7 |
| Hygromycin phosphotransferase gene (hpt) | Hygromycin phosphotransferase detoxification | Hygromycin | van den Elzen et al., 1985, Plant Mol. Biol., 5: 299-302 |
| Bleomycin resistance gene | Binding protein, detoxification | Bleomycin/phleomycin | Mazodier et al., 1985, Nuc. Acids Res., 13: 195-205; Gatignol et al., 1987, Mol. Gen. Genet., 207: 342-8 |
| Sulphonamide resistance gene (sull) | Dihydropteroate synthase, detoxification | Sulfadiazine/asulam | Guerineau et al., 1990, Plasmid, 23: 35-41; Guerineau et al., 1990, Plant Mol. Biol., 15: 127-36 |
| II. Herbicides | | | |
| Csr1-1 gene | Acetolactate synthase, insensitive | Chlorsulfuron (sulphonylurease) | Haughn & Somerville, 1986, Mol. Gen. Genet., 204: 430-4; Haughn et al., 1988, Mol. Gen. Genet., 211: 266-271 |
| aroA gene | EPSP synthase, sensitive and insensitive | Glyphosate | Rogers et al., 1983, Appl. Environ. Microbiol., 46: 37-43; Stalker et al., 1985, J. Biol. Chem., 260: 4724-8 |
| psbA gene | Q. protein, insensitive | Atrazine | Goloubinoff et al., 1984, Nuc. Acids Res., 12: 9489-96; Sato et al., 1988, Mol. Gen. Genet., 214: 358-60 |
| bar gene | Phosphinothricin acetyltransferase, detoxification | Phosphinothricin, bialaphos | Thompson et al., 1987, EMBO J., 9: 2519-23 |
| bxn gene | Nitrilase, detoxification | Bromoxynil | Stalker et al., 1988, J. Biol. Chem., 263: 6310-4 |
| dehl gene | Dehalogenase, detoxification | Dalapon | Busto et al., 1992, Sci. Total Environ., 123-124: 267-77 |
| tfd gene | 2,4-dichlorophenoxyacetate monoxygenase, detoxification | 2,4-D | Vedler et al., 2000, Gene, 245: 161-8 |

TABLE 1-continued

List of Selectable and Screenable Markers

| Type or Source of Marker | Enzyme/Mode of Action | Selection Agent/Substrate | Reference |
|---|---|---|---|
| III. Metabolic agents | | | |
| dhfr gene (bacterial/mouse) | Dihydrofolate reductase, insensitive | Methotrexate | Nakamura & Littlefield, 1972, J. Biol. Chem., 247: 179-87; Eichholtz et al., 1987, Somat. Cell Mol. Genet., 13: 67-76 |
| ocd gene | Ornithine cyclodeaminase | L-ornithine | Schindler et al., 1989, J. Bacteriol., 171: 847-54 |
| B. Scorable/assayable markers | | | |
| nos/ocs genes | Nopaline/octopine synthase | Nopaline/octopine | Yang et al., 1987, Anal. Biochem., 160: 342-5 |
| lacZ gene | β-galactosidase (β-gal), color reaction | X-gal | Pardee et al., 1959, J. Mol. Biol., 1: 165-78 |
| uidA gene | β-glucuronidase (GUS), color reaction | X-glu | Jefferson et al., 1986, PNAS USA, 83: 8447-51 |
| luc gene | Luciferase, light emission | Luciferin | Wood & DeLuca, 1987, Anal. Biochem., 161: 501-7 |
| lux gene | Luciferase, light emission | Hydrocarbon compounds | Boivin et al., 1988, Mol. Gen. Genet., 213: 50-5 |
| Streptomycin phosphotransferase gene | Streptomycin phosphotransferase, detoxification | Streptomycin | Boronin et al., 1979, Antibiotiki, 24: 585-90 |
| Chloramphenicol acetyltransferase gene | Chloramphenicol acetyltransferase, detoxification | Chloramphenicol | Shaw & Brodsky, 1968, J. Bacteriol., 95: 28-36 |

The cloning procedure described herein for mtDNA takes advantage of the fact that DNA must be circular in order to replicate in E. coli and that the mtDNA genome is typically the only circular DNA in most eukaryotic cells. Since the transposition reaction does not circularize linear DNA, the genomic DNA fragments and broken mtDNA fragments that invariably contaminate mtDNA preparations are not cloned by this procedure and so the background is very low. The replication ori and selectable marker are also inserted at random locations and orientations throughout the mitochondrial genome and so many different clones are generated in the same experiment. The most stable of these resulting constructs are readily identified during the initial plasmid analysis as those that have faithfully replicated the mitochondrial genome in E. coli.

Representative eukaryotic cells that can be made transmitochondrial for exogenous mitochondrial genomes include yeast cells, mammalian cells, avian cells, bovine cells, porcine cells, and plant cells. Mammalian cells include, but are not limited to, rodent cells, primate cells, and human cells. Methods of culturing yeast cells, mammalian cells, avian cells, bovine cells, and porcine cells are known in the art. See, for example, Cell and Tissue Culture: Laboratory Procedures, Doyle et al. eds, John Wiley & Sons, 1998; Harrison & Rae, General Techniques of Cell Culture, Harris, ed., Cambridge University Press, 1997; Basic Cell Culture: A Practical Approach, 2nd Ed., Davis, ed., Oxford Press, 2002; and Griffiths & Doyle, Mammalian Cell Culture: Essential Techniques, John Wiley & Sons, 1997.

The invention further provides for cells containing viable mitochondrial genomes. "Viable mitochondrial genomes" refer to mitochondrial genomes that can be replicated (e.g., that are maintained through multiple rounds of cell division). Maintenance of exogenous mitochondrial genomes usually requires the presence of one or more species-specific nuclear genes (e.g., encoding a mitochondrial replication factor). "Transcriptionally active" refers to a mitochondrial genome that, under the appropriate conditions, can be partially or entirely transcribed. Transcription of mitochondrial genomes generally requires the presence of one or more species-specific nuclear genes (e.g., encoding a mitochondrial transcription factor). "Species-specific" means that the nuclear genes, whether for replication or transcription, originate from the same species from which the mitochondrial genomes originated, or a species very closely related thereto.

Transmitochondrial Cells and Organisms, and Methods of Making Such Cells and Organisms The invention provides for methods of introducing an isolated mammalian mitochondrial genome into a mitochondrion. As discussed above, the mitochondrial genome can be introduced into a purified mitochondrion or into a mitochondrion within a cell. Methods of introducing DNA into purified mitochondria are known in the art and generally utilize electroporation. Methods of introducing mitochondrial genomes into mitochondria in a cell have proven much more difficult. The present invention describes methods of introducing an exogenous mitochondrial genome into a mitochondrion in a cell, as well as methods of replicating and transcribing the exogenous mitochondrial genome.

The methods of the invention have been exemplified herein by introducing mouse mitochondrial genomes into endogenous yeast mitochondria, but the methods are applicable and amenable to other eukaryotic organisms as well. For example, to make mammalian cells transmitochondrial only requires appropriate tissue culture conditions and appropriate selectable or screenable markers. Both tissue culture conditions of mammalian cells and selectable and/or screenable markers suitable for use in mammals (see Table 1 above) are well known in the art.

According to the methods of the invention, exogenous isolated mitochondrial genomes can be introduced into mitochondria in a cell using particle bombardment or any comparable technique that allows the exogenous mitochondrial genomes to pass through both mitochondrial membranes. Particle bombardment conditions for introducing DNA into endogenous mitochondria have been described (see, for example, Johnston et al., 1988, Science, 240: 1538-1541; Fox et al., 1988, PNAS USA, 85: 7288-7292), and differ little from the particle bombardment conditions for introducing DNA into plant cells.

Alternatively, exogenous mitochondrial genomes can be introduced into endogenous mitochondria via fusion and/or conversion of mitochondria by transferring the exogenous transgenomic mitochondria containing the mitochondrial genome of interest into eukaryotic cells (e.g., by microinjection of transgenomic mitochondria). In the case of fusion, the two membranes (inner and outer) of one mitochondria fuse with that of another, forming long, thin, branched "mitochondrial networks" from which mitochondria can be transiently split off (i.e., fission). Fission and fusion create a dynamic mitochondrial network system in the cell. In the case of conversion, the exogenous mitochondrial structures are gradually converted to endogenous structures as their protein and lipid components are replaced with those generated by the host cell. Following fusion and/or conversion, the exogenous mitochondrial genome of interest is maintained in endogenous mitochondria. Therefore, the transgenomic mitochondria containing the mitochondrial genomes of interest can be used essentially as carriers or delivery vehicles, and their structure in the newly-formed transmitochondrial cell is transient. Prior to this invention, fusion or conversion could only be performed with closely related species.

Irrespective of the mechanism of uptake (fusion or conversion), transmitochondrial cells or organisms can be generated using, for example, the transgenomic yeast mitochondria described herein. Transgenomic yeast mitochondria can be generated using, for example, particle bombardment, and purified using, for example, a sucrose gradient, and introduced into non-yeast eukaryotic cells (e.g., by microinjection). Yeast cells are particularly useful carriers or delivery vehicles for exogenous mitochondrial genomes because yeast cells have a fairly promiscuous replication system. As discussed above, the mitochondrial proteins from the transgenomic yeast mitochondria are exogenous to eukaryotic host cells and are eventually replaced by mitochondrial proteins endogenous to the eukaryotic cells. The methods of the invention, therefore, provide several approaches for producing an eukaryotic cell containing endogenous mitochondria that, themselves, contain exogenous mitochondrial genomes.

There are many diseases caused by mutations in the mitochondrial genome. See, for example, Dahl & Thorburn, 2001, Am. J. Med. Genet., 106:1-3; Thorburn & Dahl, 2001, Am. J. Med. Genet., 106: 102-14; and Dimauro & Schon, 2001, Am. J. Med. Genet., 106: 18-26. Using the methods of the invention, mitochondrial genomes containing a mutation can be introduced into the mitochondria of an egg or an embryo using particle bombardment as described herein. Alternatively, a mutant mitochondrial genome can be introduced into mitochondria of an egg or an embryo by a fusion-like process similar to that described above. If mitochondrial genomes are introduced into mitochondria of an embryo, the embryo is usually an early-stage embryo (e.g., generally 4-6 cells) so that the majority of cells carry mitochondria containing the mutant mitochondrial genomes. Techniques to fertilize an egg and grow the resulting embryo to an organism, particularly with model organisms such as Drosophila, Zebrafish (Danio rerio), mice, rats, and primates, as well as with domestic animals, are well known in the art. See, for example, McEvoy, 2003, Reprod. Domest. Anim., 38: 268-75; Hearn, 2001, Reprod. Fertil. Dev., 13: 517-22; and Ishiwata et al., 2001, Hum. Cell, 14: 283-91.

The invention provides for a transmitochondrial organism such as a mammal that contains exogenous isolated mitochondrial genomes. The mitochondrial genomes can be isolated from mitochondria originating from an individual afflicted with a disease, or mitochondrial genomes can be manipulated recombinantly using standard techniques such as site directed mutagenesis, saturation mutagenesis, or PCR mediated mutagenesis to contain either a specific or a random mutation. Any of a number of mammals can be used to generate a transmitochondrial mammal containing exogenous mutant mitochondrial genomes. Useful animals include, but are not limited to, mice, rat, or primates. The invention describes methods of making model organisms having mitochondria-originating diseases.

Methods of the invention also provide for a transmitochondrial organism (e.g., an animal or a plant) containing exogenous isolated mitochondrial genomes. For example, a mitochondrial genome can be manipulated to include nucleic acids encoding enzymes involved in the production of particular amino acids and/or vitamins, for example, those that are not naturally produced by an organism. A transmitochondrial organism containing mitochondria that, in turn, contain the engineered mitochondrial genome can make such amino acids and/or vitamins on their own. The diet of such a transmitochondrial organism, for example, would not need to be supplemented with such amino acids and/or vitamins.

Such transmitochondrial organisms are amenable to the production of such compounds because of the high number of mitochondria per cell, and because many if not all of the metabolic intermediates required during synthesis reactions (e.g., co-factors) are already present in the mitochondria. Another significant advantage of using a mitochondrial genome is that multiple genes should be able to be added and co-regulated as a group, like operons in bacteria, rather than needing to individually regulate them with separate promoters as is the case with mammalian nuclear genes.

With respect to plants, plant mitochondrial genomes are generally larger than other eukaryotic mitochondrial genomes. Therefore, a vector capable of allowing manipulation of large nucleic acids such as a bacterial artificial chromosome (BAC) vector can be used when manipulating plant mitochondrial genomes. Particle bombardment techniques are well established in plants (see references cited above), as are tissue culture methods and plant regeneration methods (see, for example, Smith, Plant Tissue Culture: Techniques and Experiments, 2nd Ed., Academic Press, 2000; and Evans et al., Plant Cell Culture (The Basics), Bios Scientific Pub. Ltd., 2003).

The invention will be further described in the following examples, which do not limit the scope of the invention described in the claims.

EXAMPLES

Example 1

*Escherichia coli* Strains, Cell Lines, Plasmids, and Culture Media

*Escherichia coli* strains DH5α λatt::pirwt, DH5α λatt::pir200 (Koob et al., 1994, Ann. N.Y. Acad. Sci., 745: 1-3) and DH5α λatt::pir116 were used for maintaining plasmids containing the R6K γ origin of replication (γ-ori). p2CγCmR (Koob et al., 1994, Ann. N.Y. Acad. Sci., 745:1-3), which contains the γ-ori and a chloramphenicol resistance gene (CmR), was used as a template for making a transposon DNA fragment (see below). The mouse cell line LL/2 (ATCC CRL-1642) (Bertram & Janik, 1980, Cancer Lett., 11: 63-73) was grown in DMEM (Life Technologies, Rockville, Md.) in the presence of heat-inactivated 10% fetal bovine serum at 37° C. in a humidified 10% $CO_2$ incubator. The mtDNA-less ρ0 LL/2 cell line described herein, a derivative of LL/2 cells, was grown in DMEM supplemented with 10% fetal bovine serum, 50 μg/ml uridine and 0.1 mg/ml pyruvate.

Example 2

Isolation of mtDNA-Less (ρ0) LL/2 Cell Line

The mtDNA-less ρ0 LL/2 cell line was isolated by a modification of a method previously described (King & Attardi, 1989, Science, 246: 500-3; Bai & Attardi, 1998, EMBO J., 17: 4848-58), which involves treatment of LL/2 cells with high concentrations of ethidium bromide. LL/2 cells were exposed to 5 μg/ml ethidium bromide for 4 weeks in medium supplemented with 50 μg/ml uridine and 0.1 mg/ml pyruvate. After 4 weeks, clonal ρ0 LL/2 cell lines were obtained by diluting these ethidium bromide-treated cells to single cells per well on 96-well plates. The clonal cells were then cultured in normal medium supplemented with 50 μg/ml uridine and 0.1 mg/ml pyruvate. The ρ0 state of the cloned cells was verified by a PCR assay using L-strand (5'-ACC CAA CGC GGC AAA CTA ACC-3' (SEQ ID NO:1)) and H-strand (5'-TCT TGT TCG TCT GCC AGG CT-3' (SEQ ID NO:2)) primers and by assaying for the unique growth requirements of the ρ0 cells (King & Attardi, 1996, Methods Enzymol., 264: 304-13).

Example 3

DNA Manipulation

Mini-scale preparations of plasmid DNA were prepared by the alkaline lysis method (Sambrook et al., 1989, Molecular Cloning: A Laboratory Manual, 2nd Ed., Cold Spring Harbor Laboratory Press, Cold Spring Harbor, N.Y.) and large quantities of plasmid DNA were prepared by the PEG precipitation method and other recombinant DNA techniques were performed essentially as previously described (Sambrook et al., supra). Restriction enzymes and T4 DNA ligase were purchased from New England Biolabs (Beverly, Mass.) and used as recommended by the manufacturer. AmpliTaq DNA polymerase was purchased from Applied Biosystems (Branchburg, N.J.) and deoxyoligonucleotides (oligos) were synthesized by Life Technologies (Rockville, Md.) or IDT (Coralville, Iowa). Ampicillin (Amp), tetracycline and chloramphenicol (Cm) were used at concentrations of 50, 12.5 and 12.5 μg/ml, respectively.

Example 4

Isolation of mtDNA from Mouse Liver

The liver of a freshly killed mouse was removed and placed in cold isolation medium (0.32 M sucrose, 1 mM potassium EDTA, 10 mM Tris-HCl pH 7.4). All subsequent steps were performed at 4° C. or on ice. The tissue was minced with scissors and rinsed several times with the same medium. The chopped tissue was suspended in isolation medium (4 ml/g liver) and homogenized in a Potter-Elvehjem tissue grinder (Kontes Glass Co., Vineland, N.J.). The homogenate was transferred to 50 ml centrifuge tubes and centrifuged at low speed (1000 g, 5 min). The supernatant was then centrifuged at high speed (13 000 g, 20 min). The resultant supernatant was discarded, the pellet was resuspended in 5 ml of DNase I buffer (210 mM mannitol, 70 mM sucrose, 5 mM Tris-HCl pH 7.4, 10 mM MgCl2) containing 0.5 mM phenylmethylsulfonyl fluoride. The suspension was incubated with 4000 Kunitz units of DNase I (Sigma) at 37° C. for 1 h. After incubation, the suspension was washed three times in 10 vol of washing buffer (210 mM mannitol, 70 mM sucrose, 5 mM Tris-HCl pH 7.4, 10 mM EDTA) by centrifugation at 13 000 g for 20 min. The washed pellet was resuspended in 5 ml of sucrose-TE buffer (20% sucrose, 50 mM Tris-HCl pH 7.4, 10 mM EDTA) and loaded on top of sucrose layers consisting of 15 ml of 1.5 M sucrose (lower layer) and 15 ml of 1.0 M sucrose (upper layer), both containing 10 mM Tris-HCl pH 7.4, 5 mM EDTA. After centrifugation at 25,000 rpm for 30 min in a Beckman SW28 rotor, the interface fraction (red-brown color) between the 1.0 and 1.5 M sucrose gradients was collected and washed twice with 4 vol of washing buffer by centrifugation at 18,000 g for 20 min. The mitochondrial pellet was suspended in 3 ml of STE buffer (100 mM NaCl, 10 mM EDTA, 50 mM Tris-HCl pH 7.4) and incubated with 330 μl of 10% SDS and 400 μl of proteinase K (10 mg/ml) at 50° C. for 3 h. After incubation, the digest was extracted with 3 ml of phenol/chloroform saturated with TE (10 mM Tris-HCl pH 7.4, 1 mM EDTA) by shaking gently for 10 min and the extraction was repeated with 3 ml of chloroform. The DNA in the aqueous phase was precipitated by the addition of 370 μl of 3 M sodium acetate and 6 ml of absolute ethanol (30 min at −20° C.). The DNA was collected by centrifugation, washed with 3 ml of 70% ethanol, dried, and resuspended in TE.

Example 5

In Vitro Transposon Insertion Reaction

A synthetic transposon in which the γ-ori and a chloramphenicol resistance gene are flanked by Tn5 mosaic ends (ME) was generated by a PCR using BamHI-linearized p2Cγ CmR as template and the primers MESalCmR (5'-CTG TCT CTT ATA CAC ATC TGT CGA CAG AAG CCA CTG GAG CA-3' (SEQ ID NO:3); ME sequence italicized, SalI restriction site underlined) and MESma γ ori (5'-CTG TCT CTT ATA CAC ATC TCC CGG GCT MT TCT GTC AGC CGT T-3' (SEQ ID NO:4); SmaI restriction site underlined). A total of 30 amplification cycles were performed: 1 min at 95° C., 1 min at 55° C., followed by 90 s at 72° C. PCR products were isolated from low melting point agarose gels (FMC, Rockland, Me.) using AgarACE™ (Promega, Madison, Wis.). For the in vitro transposon insertion reaction, a purified hyperactive Tn5 transposase (EZ::TN; Epicentre, Madison, Wis.) was used in a reaction consisting of 1 U transposase, 200 ng mouse mitochondrial DNA and 10 ng PCR-amplified transposon in the buffer provided by the supplier. After incubating the reaction mixture for 2 h at 37° C., the reaction was terminated by adding 1 μl of the supplied 10× stop solution and by heating at 70° C. for 10 min. An aliquot of 1 μl of the in vitro transposon insertion reaction mixture was used for electrotransformation of DH5α λatt::pirwt.

Example 6

Figure 2:
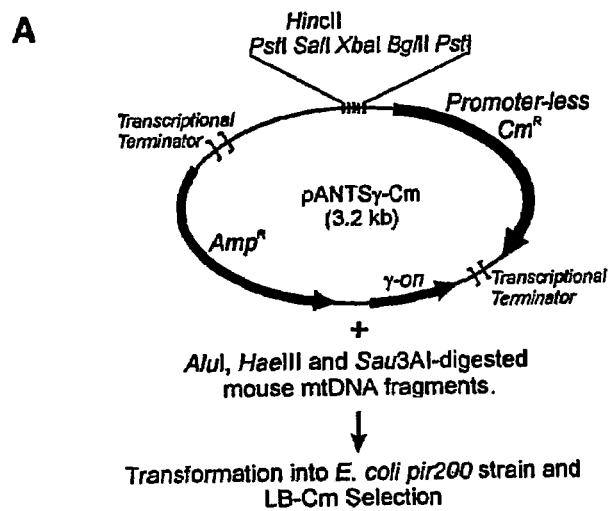
FIG. 2 shows the identification of mitochondrial DNA fragments that serve as transcriptional promoters in *E. coli*.
Figure 2:
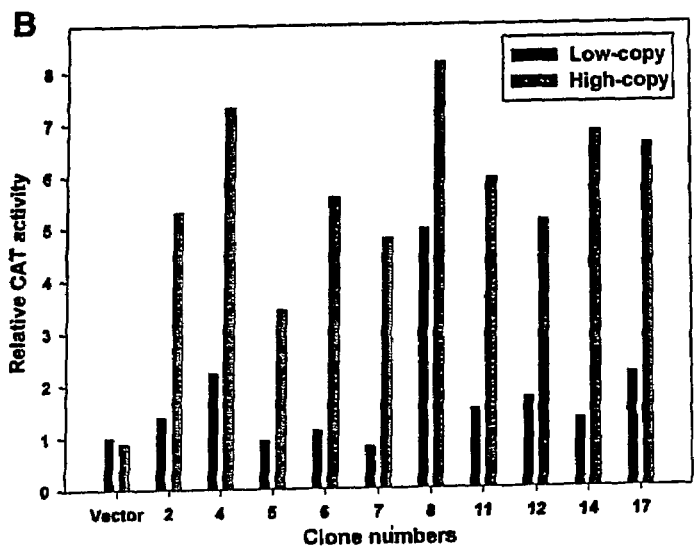

Cloning of mtDNA Fragments with Promoter Activity in *E. Coli* and the Chloramphenicol Acetyltransferase (CAT) Assay Mouse mtDNA digested with AluI, HaeIII and Sau3AI was ligated into the HincII and BglII sites 5' of the promoter-less chloramphenicol acetyltransferase gene (CAT, CmR) of the 'promoter trapping' vector pANTSγ-Cm (FIG. 2A). The ligation mixture was transformed into *E. coli* strain DH5α λatt::pir200 and recombinant clones were selected on Luria broth (LB)-Cm plates (12.5 µg/ml Cm). DNA isolated from these colonies was sequenced and retransformed into DH5α λatt::pirwt (LB-Amp selection). The CAT activity from the same recombinant clones was assayed in both the pir200 and pirwt strains grown in LB-Amp medium to an optical density of ~0.6 at 600 nm. CAT activity was assayed using the FAST CAT® Green (deoxy) Chloramphenicol Acetyltransferase Assay Kit (Molecular Probes Inc., Eugene, Oreg.) according to the manufacturer's instructions. A PhosphorImager Storm 840 (Molecular Dynamics, Sunnyvale, Calif.) system was used to measure band intensity of the acetylated products after fractionating on a thin layer chromatography plate (Merck KGaA, Darmstadt, Germany). Values of the intensities were calculated relative to the CAT activity of the vector-only low copy control sample.

Example 7

Electroporation of Mitochondria

Exponentially growing LL/2 cells were harvested by centrifugation, washed twice with 1 mM Tris-HCl pH 7.0, 0.13 M NaCl, 5 mM KCl and 7.5 mM MgCl2. The cell pellet was resuspended in half the cell volume with 1/10×IB (4 mM Tris-HCl pH 7.4, 2.5 mM NaCl, 0.5 mM MgCl2) and the cells were broken using a Pellet Pestle tissue grinder (Kontes Glass Co.). The homogenate was mixed with a one-ninth volume of the packed cell volume of 10×IB (400 mM Tris-HCl pH 7.4, 250 mM NaCl, 50 mM MgCl2) resulting in a buffer concentration of roughly 1×IB (40 mM Tris-HCl pH 7.4, 25 mM NaCl, 5 mM MgCl2). The unbroken cells and nuclei were removed by two consecutive low speed centrifugations (2000 rpm for 5 min). The supernatant was placed into new 1.5 ml Eppendorf tubes and centrifuged at full speed for 10 min to obtain a crude mitochondrial pellet. Mitochondria were rinsed once with 500 µl of 1×IB, centrifuged again at full speed for 10 min and resuspended into 0.33 M sucrose/10% glycerol (at a concentration of 100 mg mitochondrial protein/ml) for electroporation. Electroporations were performed essentially as described (Collombet et al., 1997, J. Biol. Chem., 272: 5342-7). An aliquot of 10 µg of cloned mouse mtDNA was added to 50 µl of 100 mg/ml mitochondrial suspension and the mixture was transferred into a cold electroporation cuvette (0.1 cm gap cuvette; Bio-Rad). Electroporation was carried out using a Bio-Rad Gene Pulser at a capacitance of 25 µF, a resistance of 400Ω and a field strength of 10-16 kV/cm. After electroporation, 1 ml of incubation buffer (40 mM Tris-HCl pH 7.4, 25 mM NaCl, 5 mM MgCl2, 10% glycerol) was added to the electroporation cuvette. The electroporated mitochondria were rapidly mixed by pipetting, transferred to a new Eppendorf tube and washed three times with incubation buffer by centrifugation.

Example 8

In Organello RNA Synthesis of Electroporated Mitochondria and RT-PCR Analysis

For in organello RNA synthesis (Gaines, 1996, Methods Enzymol., 264: 43-9), the final mitochondrial pellet was resuspended in 50 µl of incubation buffer (10% glycerol, 40 mM Tris-HCl pH 7.4, 25 mM NaCl, 5 mM MgCl2, 1 mM pyruvate, 1 mM ATP and 1 mg/ml BSA) and incubated at 37° C. for 2 h. After incubation, the mitochondrial suspension was pelleted at full speed in a microcentrifuge for 10 min and washed twice with incubation buffer. The pellets were suspended in 200 µl of DNase I buffer (10% glycerol, 10 mM Tris-HCl pH 8.0, 1 mM MgCl2) and incubated with 200 Kunitz units of DNase I (Sigma) at 37° C. for 30 min. After incubation, the mitochondria were pelleted and washed twice with washing buffer (10% glycerol, 10 mM Tris-HCl pH 7.4, 1 mM EDTA) to inactivate and remove the nuclease. The mitochondrial samples were lysed with 300 µl of lysis buffer (0.5% SDS, 10 mM Tris-HCl pH 7.4, 150 mM NaCl, 1 mM EDTA) and incubated with 100 µg proteinase K for 15 min at 37° C. Phenol extraction was then performed, total mitochondrial nucleic acids were collected by ethanol precipitation and residual DNA contaminants were removed using RNase-free DNase I (Promega) as directed by the manufacturer. RT-PCR was carried out using 16S rRNA-specific or ND6-specific primers. RT-PCR analysis was carried out using a SuperScript First-Strand Synthesis system (Life Technologies) and the following primers: CmR-F (5'-GTA CCT ATA ACC AGA CCG TTC AGC-3' (SEQ ID NO:5)), CmR-R (5'-CAG CGG CAT CAG CAC CTT GTC-3' (SEQ ID NO:6)), 16S rRNA-F (5'-GCA GCC ACC AAT AAA GAA AG-3' (SEQ ID NO:7)), 16S rRNA-R (5'-GGA CCC TCG TTT AGC CGT TC-3' (SEQ ID NO:8)), MusMt-MIulA (5'-AGG TGG ATT ATT TAT AGT GTG ATT ATT GCC-3' (SEQ ID NO:9)), ND6-F (5'-GGA GAT CTT GAT GTA TGA GGT TGA TGA TGT TGG A-3' (SEQ ID NO:10)) and ND6-R (5'-CCC GCA AAC AAA GAT CAC CC-3' (SEQ ID NO:11)). The following PCR cycle parameters were used for each of the RT-PCR reactions: 95° C. for 5 min, followed by 30 cycles of 95° C. for 30 s, 60° C. for 45 s and 72° C. for 30 s, and finally 72° C. for 10 min. 16S rRNA-R and ND6-R primers were used as gene-specific primers for the first strand synthesis of 16S rRNA and ND6 transcription, respectively, and the 16S rRNA-F and MusMt-MIulA primer set or ND6-F and ND6-R primer set was used for subsequent PCR amplification, respectively. Expected band sizes of the RT-PCR products were 232 bp for 16S rRNA and 123 bp for ND6, respectively.

Example 9

Cloning the Mouse Mitochondrial Genome in *E. coli*

A scheme was devised for cloning complete mitochondrial genomes in *E. coli* that uses an in vitro transposition reaction to insert an *E. coli* origin of DNA replication (ori) and selectable marker at random locations into circular mtDNA. To make a synthetic transposon containing the γ-ori from the R6K plasmid (Kolter & Helinski, 1982, J. Mol. Biol., 161: 45-56; Shafferman et al., 1982, J. Mol. Biol., 161: 57-76) and the CmR gene, a PCR amplification was performed using linearized plasmid p2C γ CmR as template and the PCR primers MESalCmR and MESma γ ori. These primers contain the 19 bp Tn5 transposase recognition sequences (mosaic end or ME) and the unique restriction sites for SalI and SmaI, respectively, at their 5' ends and plasmid-specific sequences at their 3' ends. The 1.5 kb PCR-amplified transposon, therefore, consisted of the CmR marker and the γ-ori flanked by inverted Tn5 ME sequences at each of its ends. To perform the in vitro transposition reaction, this linear synthetic transposon was incubated with hyperactive Tn5 transposase and isolated, circular mouse mtDNA. The products from this transposition reaction were electroporated into an *E. coli* strain containing a chromosomal copy of the R6K pir gene, which encodes the replication initiator protein needed for γ-ori replication (Kolter & Helinski, supra; Shafferman et al., supra), and transformants were selected on Cm plates.

Three transposon-inserted mouse mtDNA clones obtained using this cloning strategy were characterized by restriction enzyme mapping and sequencing. FIG. 1 shows the schematic representation of the mouse mtDNA clones. All of the transposons were inserted into the mouse mtDNA in the same orientation. When the transposon junctions of these clones were sequenced using vector-specific sequencing primers, it was found that the transposons were inserted into the ND1, COXII and ND5 genes on the mouse mtDNA at nucleotides 3347, 7688 and 13371, respectively. Tn5 transposition reactions typically generate a 9 bp target duplication immediately flanking the transposon insertion site and these sequence duplications were found in each of the mouse mtDNA clones. Extensive sequencing of these clones identified several sequence polymorphisms present in the mtDNA of the mouse strain used as the source of the mtDNA but further confirmed the overall sequence integrity of the constructs.

Example 10

Comparison of the Stability of Mouse mtDNA Clones in *E. coli* at Low and High Copy Number To examine the stability of the cloned mouse mtDNA in *E. coli*, the three mapped mouse mtDNA clones were transformed into one of two *E. coli* strains. One of these strains contained the wild-type pir gene (pirwt) in the chromosome and replicated the mtDNA clones at a moderately low number of copies/cell (~10-15 copies/cell), and the other strain contained a mutant pir gene (pir116) (Greener et al., 1990, Mol. Gen. Genet., 224: 24-32) that replicated the clones at a relatively high number of copies/cell (200 copies).

After transforming the mtDNA plasmids into the pirwt strain, cultures were grown in LB medium at 30 or 37° C., plasmid DNA was isolated at regular time intervals and the restriction patterns of these DNA preparations were compared. No deletions or rearrangements were observed in the mouse mtDNA fragments even after several days of culture at either slow growth (30° C.) or rapid growth (37° C.) temperatures. When the mouse mtDNA clones were transformed into the pir116 strain, however, the transformation efficiency using the same standard chemical transformation method was dramatically lower than that seen with the pirwt strain (Table 2). The mtDNA clones were electroporated into the pir116 strain in order to obtain more transformants, and restriction analyses of plasmid DNA isolated from the few colonies that were formed was performed. It was found that almost all of these colonies contained plasmids in which all or most of the mouse mtDNA sequence was deleted.

TABLE 2

Transformation efficiency of the mouse mtDNA clones in two different *E. coli* strains

| Plasmid | Transformation efficiency DH5α λatt::pirwt[a] | Colonies/µg DNA DH5α λatt::pir116[a] |
|---|---|---|
| P2CγCm[R] | $1.2 \times 10^5$ | $1.3 \times 10^5$ |
| pMusMtTN-ND1 | $7.5 \times 10^3$ | 1 |
| pMusMtTN-COXII | $9.0 \times 10^3$ | 2 |
| pMusMtTN-ND5 | $8.5 \times 10^3$ | 1 |

[a]*Escherichia coli* strain.

Example 11

Identification of mtDNA Fragments with Transcriptional Promoter Activity in *E. coli*

It was hypothesized that transcription of mtDNA in *E. coli* was a likely underlying cause of the apparent toxicity of the mtDNA sequences at high copy number. To test this hypothesis, mtDNA fragments were cloned into a 'promoter-trap' vector designed to directly select recombinant clones in which a promoter-less CmR (CAT) gene is transcribed only if an inserted DNA fragment has promoter activity (FIG. 2A). AluI, HaeIII and Sau3AI were used to digest mouse mtDNA into relatively small fragments, which were cloned into the HincII or BglII sites upstream of the CAT gene in pANTS γ-Cm. Recombinant clones with inserts that had promoter activity were selected by transforming them into an *E. coli* strain that replicated the plasmids at high copy number (pir200) and plated on LB-Cm plates. The mouse mtDNA fragments identified in this screen are listed in Table 3. The plasmids containing these inserts were transformed into the low copy *E. coli* strain (pirwt) and the CAT activity generated from each clone was measured at both low and high copy numbers (FIG. 2B). For each of the mtDNA fragment clones, the CAT activity generated in the high copy strain was significantly higher than that generated in the low copy strain, with many of the fragments only producing background levels of CAT activity at low copy numbers.

TABLE 3

Functional *E. coli* promoter-like sequences identified in mouse mtDNA

| Clone No. | Restriction Fragment | Position in mouse mtDNA[a] |
|---|---|---|
| 1 | HaeIII | 2216-2857 |
| 2 | HaeIII | 2857-3336 |
| 3 | Sau3AI | 4276-5887 |
| 4 | HaeIII | 4671-6622 |
| 5 | Sau3AI | 5884-5991 |
| 6 | AluI | 6336-6717 |
| 7 | AluI | 7709-8254 |
| 8 | Sau3AI | 8165-8940 |
| 9 | AluI | 8491-9045 |
| 10 | HaeIII | 8812-9757 |
| 11 | AluI | 9045-9138 |
| 12 | AluI | 10978-11083 |
| 13 | HaeIII | 11119-11193 |
| 14 | Sau3AI | 12028-13403 |
| 15 | AluI | 13844-14913 |
| 16 | Sau3AI | 14749-15333 |
| 17 | HaeIII | 15190-15740 |

[a]Nucleotide numbering based on GenBank Accession No. NC_001569

Example 12

Modification of pMusMtTN Plasmids in *E. coli*

Numerous modifications were made to the pMusMtTN plasmids using standard cloning techniques. It was determined that these plasmids are amenable to most alterations as long as the recombinant clones were propagated in pirwt *E. coli* strains. To determine if any segments of the mouse mtDNA genome contain sequences that might make modifying or subcloning these segments difficult, four segments spanning the entire mtDNA sequence were each isolated and subcloned. The appropriate clones were digested with the restriction enzyme pairs BglII/MluI, MluI/BspEI, BspEI/SphI, and SphII/BglII (see FIG. 1), the smaller DNA segments between these restriction sites were isolated and cloned into a plasmid with a replication ori from pBR322. The expected subclones were obtained from each of these segments. These subcloned fragments were then recloned back into the full pMusMtTN constructs. No problems were experienced with any of these segments except the SphI-BglII fragment, from which only a small number of recombinant clones were obtained. To further localize the source of this cloning difficulty, this mtDNA segment was subdivided into SphI-XhoI and XhoI-BglII fragments. It was found that the SphI-XhoI segment could be cloned with a normal level of efficiency whereas the number of clones obtained from the XhoI-BglII segment was once again noticeably reduced. The XhoI-BglII segment in the clones was sequenced and found to still contain the full, unaltered mtDNA sequence.

Example 13

Figure 3:
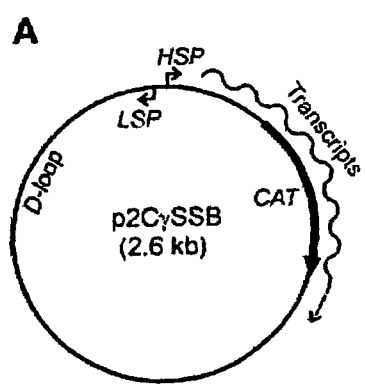
FIG. 3 is a schematic representation of p2CγSSB, a control plasmid used to examine DNA transcription assay by in organello RNA synthesis.

In Organello RNA Synthesis from Electroporated Mitochondria Using Cloned Mouse mtDNA p2C γSSB (FIG. 3) was constructed as a control template to develop a RT-PCR assay for transcription of foreign DNA introduced into purified mitochondria. This plasmid was designed so that the CAT gene of the plasmid would be transcribed from the mouse mitochondrial H-strand promoter (HSP) once the construct was introduced into physiologically active mitochondria. p2C γSSB also contain the D-loop region and L-strand promoter (LSP) sequences from the mouse mitochondrial genome.

Electroporation was used to introduce p2CγSSB into wild-type and mtDNA-less (ρ0) mitochondria purified from mouse LL/2 and ρ0 LL/2 cell lines, respectively. In order to optimize the electroporation reaction, multiple electroporation reactions were performed with field strengths ranging from 10 to 16 kV/cm (25 μF capacitance, 400 resistance). The electroporated mitochondria were incubated in a buffer suitable for in organello RNA synthesis, total RNA was isolated from these mitochondria, and RT-PCR analysis was performed to identify the RNA transcribed from the electroporated DNA. For these experiments, the RNA transcribed across the CAT gene by the HSP mitochondrial promoter was analyzed using the CAT-specific primers CmR-R and CmR-F. Mitochondrial RNA transcripts were clearly detected from DNA electroporated into both wild-type and ρ0 mitochondria. Positive signals were detected for both 12 and 14 kV/cm electroporation conditions. No signal was detected in the control reactions without reverse transcriptase (−RT) or in the no electroporation controls, in which plasmid p2CγSSB was mixed with purified mitochondria without electroporation.

Once robust electroporation and transcription assay conditions had been established, the mouse mtDNA clone pMusMtTN-COXII was electroporated into purified mouse ρ0 mitochondria and in organello RNA synthesis was performed as described herein. In this experiment, RT-PCR was used to assay for the expression of the 16S rRNA and ND6 genes, which are transcribed from HSP and LSP, respectively. RNA transcripts were clearly detected from each strand of the modified mitochondrial genome electroporated into the ρ0 mitochondria. These experiments were performed using a variety of electroporation conditions. Results determined that using 16 kV/cm for the electroporation reaction most often resulted in the most efficient transfer of the 17.8 kb mouse mtDNA construct into transcriptionally active ρ0 mitochondria.

Example 14

Figure 4:
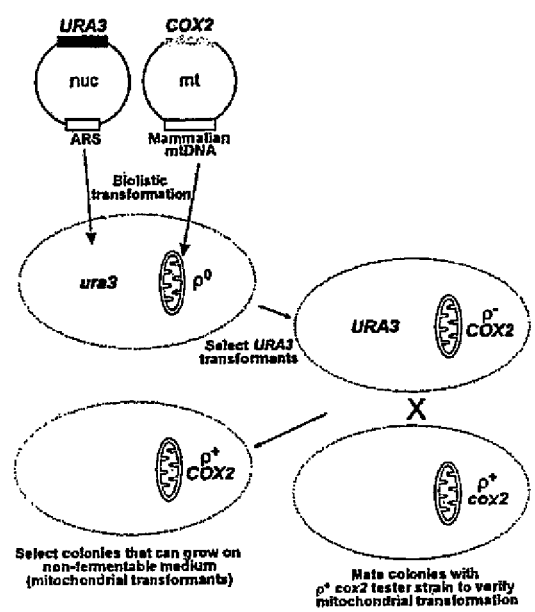
FIG. 4 is a schematic showing transformation of *S. cerevisiae* mitochondria in the cell by particle bombardment.

Full Genomic Constructs are Replicated with a High Degree of Fidelity in Yeast Mitochondria FIG. 4 shows a schematic of the methods used to make transmitochondrial yeast cells. The DNA that is targeted to the yeast mitochondria carries a wild-type copy of the yeast mitochondrial COX2 gene and is mixed with a second plasmid designated pRS426 that carries a nuclear genetic marker (URA3) and a yeast DNA replication origin (ARS) (Christianson et al., 1992, Gene, 110: 119-22; and GenBank Accession No. U03451). This DNA mixture is then combined with inert tungsten carrier particles and is introduced into a lawn of ρ0 yeast cells (MCC109ρ0 cells) plated on uracil deficient selection plates using a biolistic transformation apparatus (PDS-1000/He; BioRad) using a previously described procedure (Fox et al., 1988, PNAS USA, 85: 7288-92 and Bonnefoy & Fox, 2002, Methods Enzymol., 350: 97-111).

Yeast colonies that grew on uracil deficient selection plates after bombardment were a result of nuclear transformation with the URA3 gene. In order to find the fraction of cells (~0.1%) that have incorporated exogenous DNA into their mitochondria as well as into their nucleus, the colonies from the bombardment plate were replica plated onto a lawn of a "tester" yeast strain. This tester strain (MCC124) is of the opposite mating type than the transformed cells and has a full yeast mitochondrial genome with a point mutation in the mitochondrial COX2 gene (ρ+cox2). The mitochondrial networks of the two cell types fuse after mating, and those bombarded cells that have a functional COX2 gene in their mitochondria complement the cox2 mutation of the tester strain. These mated cells are themselves replica plated onto non-fermentable growth media on which only those mating progeny with full mitochondrial function can grow.

In initial experiments using the above-described mitochondrial transformation procedure, several different COX2 fragments were tested to determine the optimal marker. mtDNA fragments that included both the COX2 promoter and full coding frame were the easiest to score in the screening assay. Therefore, the full-length COX2 was used for most of the subsequent experiments. As noted by Fox et al. (1988, PNAS USA, 85: 7288-7292), the transcribed COX2 genes apparently complement the cox2 mutation in trans without requiring recombination between the two mitochondrial genomes. The resulting increased complementation efficiency has the added benefit of allowing the use of a color selection on the original mating plate to determine which colonies contain functional mitochondria. The ρ0 strain used in the transformations described herein has an ade2 mutation that leads to accumulation of an intermediate in the adenine biosynthesis pathway. In those cells that have fully functional mitochondria, this intermediate is converted to a red pigment and the cells turn pink. The cells that do not have mitochondrial function cannot oxidize this intermediate and the cells remain white.

Figure 5:
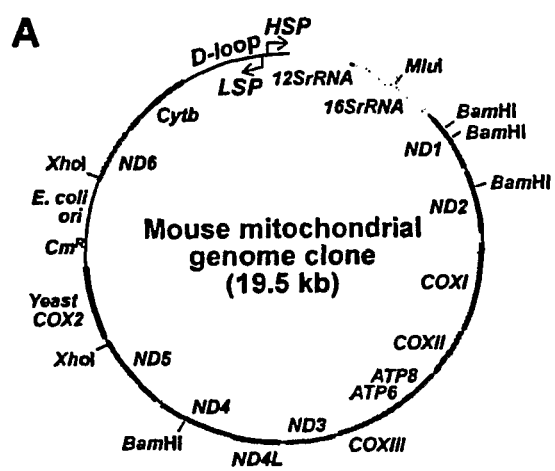
FIG. 5 shows a map of a construct containing the mouse mitochondrial genome.

To make a clone containing the full mouse mitochondrial genome without any gene disruptions, the transposon insertion in the plasmid pMusMtEZTN-ND5 was moved to regenerate the complete ND5 and ND6 genes. The plasmid pMusMtEZTN-ND5 was double-digested with XhoI and SalI, and a synthetic XhoI-SalI linker containing the 3' end-sequences of the ND6 gene and an additional FspI site was cloned between the XhoI and SalI sites. This cloning regenerated the entire ND6 gene. To regenerate an uninterrupted ND5 gene, the wild type mouse XhoI/SphI mtDNA fragment from the plasmid pMusMtEZTN-ND1 was cloned between the XhoI and SphI sites of p2CγApR-Mt. This vector contained a modified multiple cloning sites (MCS) that included the 3' end sequences of the ND5 gene from the mtDNA XhoI site to the stop codon of the ND5 gene. The NotI/SphI fragment from this construct, which contained the γ-ori and mtDNA sequences from the end of ND5 to the SphI site, was isolated and was used to replace the NotI/SphI fragment of the ND6-linker modified pMusMtEZTN-ND6 construct. A SmaI/KpnI DNA fragment containing the complete COX2 gene from yeast mtDNA was generated by PCR and introduced into the SmaI/KpnI of this plasmid clone to generate the mouse mtDNA construct used in yeast bombardment experiments (FIG. 5).

Modification of the pMusMtEZTN-ND5 results in two XhoI sites flanking the E. coli vector sequences (γ-ori+CmR) and the yeast screening marker (COX2). Digesting the vector with XhoI to remove the E. coli vector sequences and self-ligating the mitochondrial DNA sequences would allow intact and entire mouse mitochondrial genome to be recovered from this vector.

A Southern analysis of two transmitochondrial clones grown to stationary phase five times sequentially on YPD media was performed. Although a separate analysis of individual colonies isolated during this culturing process indicated that some cells do lose the mouse mitochondrial genome, no significant rearrangements or deletions were detected in the mouse genomic constructs. Although mtDNA replication in mouse mitochondria is strictly dependent on transcription, these results confirm that replication of the mouse mitochondrial genome in yeast is completely independent of transcription from the mouse mitochondrial promoters. By transferring this genome into yeast, therefore, an in vivo experimental system has been generated in which most aspects of mammalian mitochondrial transcription can be tested without jeopardizing either mitochondrial DNA integrity or cell viability.

Example 15

Species-Specific Control of Mitochondrial Transcription

Figure 6:
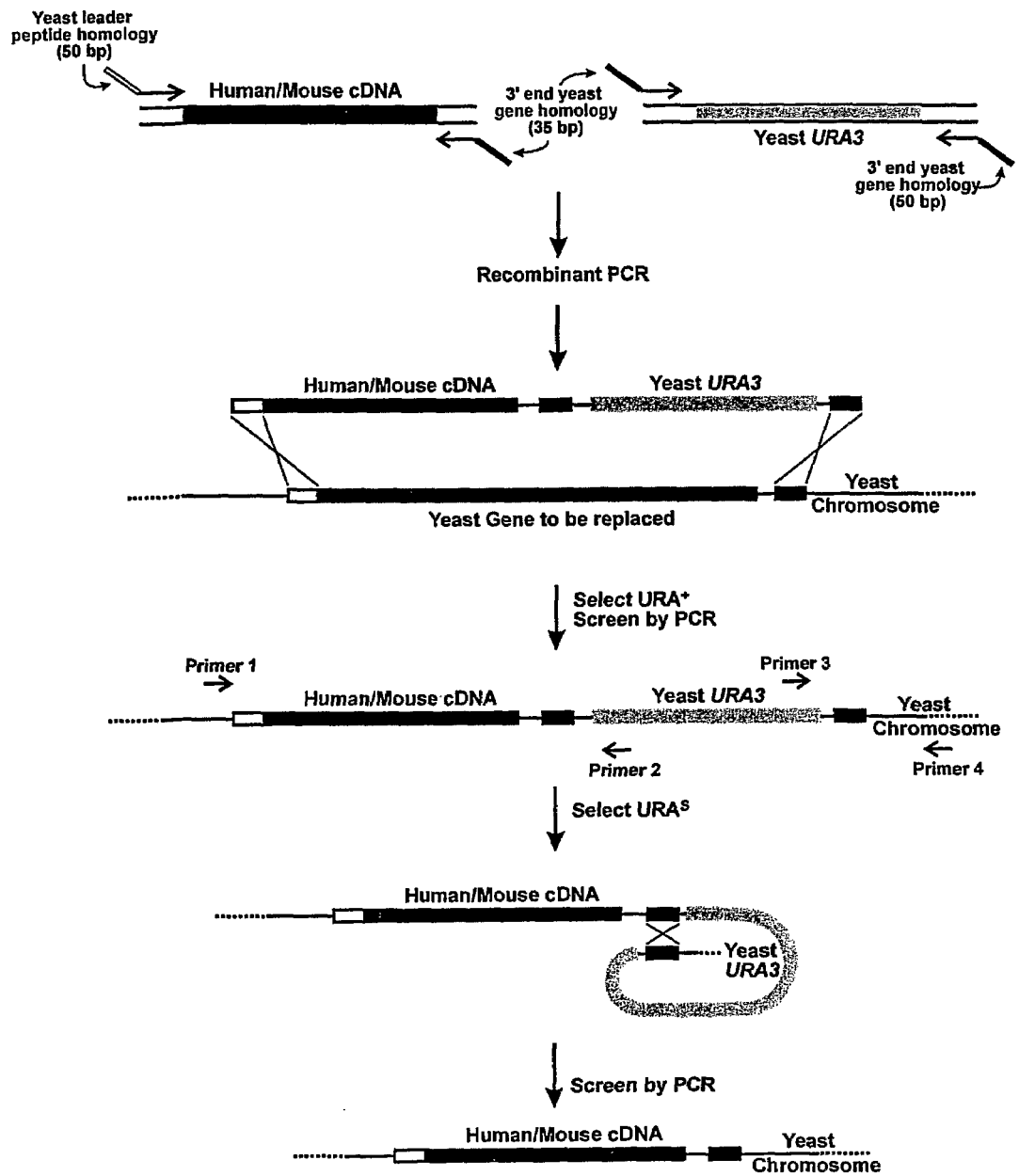
FIG. 6 shows the gene replacement strategy used to generate single gene replacement yeast strains.

The gene replacement strategy shown in FIG. 6 was used to generate single gene replacement yeast strains in which the mouse POLRMT, TFB2M, or TFAM genes were inserted in-frame immediately 3' of the mitochondrial targeting sequence of their respective homologous yeast genes. A yeast strain was also generated in which the TFB2M gene was inserted into the yeast COX4 gene. This strain was generated because the yeast homolog of TFB2M, MTF1, does not have a known mitochondrial targeting sequence, while COX4 does. The chromosomal location of each of these insertions was confirmed by PCR, and the precise recombination junctions and integrity of the mammalian transcription genes were confirmed by sequencing. Insertion strains in which the GFP gene is fused in-frame at the 3' of each of these genes were generated to confirm that the mouse transcription proteins are properly expressed and targeted to the mitochondria.

Figure 7:
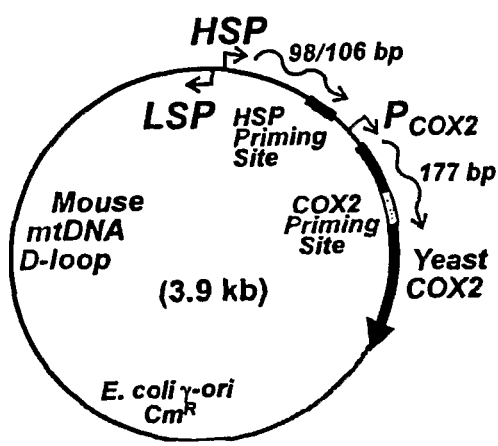
FIG. 7 shows a construct for examining in vivo transcription initiation at mitochondrial promoters.

The ρ0 haploid strains were mated with a haploid strain of opposite mating type that contains a synthetic mitochondrial DNA construct (ρ−) containing both a yeast and mouse mitochondrial promoter to determine the affect of these gene insertions on transcription from both mouse and yeast mitochondrial promoters. The E. coli plasmid used to generate this ρ-strain contains both the HSP and LSP and full D-loop region of the mouse mitochondrial genome as well as the yeast mitochondrial COX2 gene and promoter (FIG. 7).

An oligonucleotide complementary to an internal site in yeast mitochondrial C"OX2 (COX2PrEx2, 5'-ATC ATG TAA TTC TAA AAT AC-3' (SEQ ID NO:12)) or mouse mitochondrial D-loop region (LSPrEx2, 5'-TCA TGC TTG TTA GAC ATA AA-3' (SEQ ID NO:13); and T7PRO2, 5'-CCT ATA GTG AGT CGT ATT A-3' (SEQ ID NO:14)) was radiolabeled with [α-32P]ATP (3000 Ci/mmol; PerkinElmer) and T4 polynucleotide kinase (Epicenter). The labeled oligonucleotide was used as a primer in reverse transcription reactions using total yeast RNA. The labeling reaction conditions are shown below in Table 4. The components were combined, incubated at 37° C. for 30 min, and then incubated at 65° C. for 5 min to inactivate the T4 polynucleotide kinase.

TABLE 4

Labeling Reaction Conditions

| Component | Amount (µl) |
| --- | --- |
| DEPC-treated water | 12.0 |
| 10X Kinase buffer | 2.5 |
| Primer (20 uM) | 2.5 |
| [α-32P]ATP | 6.0 |
| T4 polynucleotide kinase (10 U/µl) | 2.0 |
| Total | 25.0 |

Total RNAs from yeast cultures were collected by isopropyl alcohol precipitation and residual DNA contaminants were removed using RNase-free DNase I (Promega) (Table 5). The components were combined, and incubated at 37° C. for 1 h. 1.5 µl of stop solution was THEN added, and the reaction was incubated at 65° C. for 10 min to inactivate the RNase-free DNase I.

TABLE 5

Elimination of DNA Contamination from RNA Preparations

| Component | Amount (µl) |
| --- | --- |
| Total RNA (~50 µg) | 10.0 |
| 10X DNase I buffer | 1.5 |
| RNase-free DNase I (1 U/µl) | 1.0 |
| DEPC-treated water | 2.5 |
| Total | 15.0 |

Primer extension reactions were then carried out using a SuperScript first-strand cDNA synthesis system (Life Technologies). The reaction components of the primer extension reactions are shown below in Table 6. After the reaction components were combined, the reaction was slow cooled to anneal the primers by reducing the temperature from 70° C. to less than 37° C. over a 15- to 20-minute interval. The reaction was put on ice for 1 min and the following reagents were added: 4.0 µl of 10× reverse transcriptase buffer, 4.0 µl of 0.1 M DTT, 1.0 µl of RNaseOut ribonuclease inhibitor (40 U/µl), and 5.0 µl of DEPC-treated water. The reaction was then incubated at 42° C. for 2 min, 1.0 µl of SuperScript II reverse transcriptase (200 U/µl; Invitrogen) was added, and the reaction was incubated at 42° C. for 50 min. The reaction was then terminated by heating to 70° C. for 15 min.

TABLE 6

Reaction Mix for Primer Extensions

| Component | Amount (μl) |
|---|---|
| DNase I-treated RNA | 16.5 |
| 10 mM dNTPs | 2.0 |
| 2 uM labeled primer | 2.5 |
| DEPC-treated water | 4.0 |
| Total | 25.0 |

One-tenth volume (~4 μl) of 3 M sodium acetate and three volumes (120 μl) of ethanol were added into each sample and the samples were chilled at −70° C. from 10 min. The primer extension products were then precipitated by centrifugation (13,200 rpm for 30 min) and washed with 80% ethanol for 5 min. The products were dried and resuspended with TE containing RNase A (40 μg/ml).

Each sample was heated to 92° C. for 5 min to denature the primer extension products after adding 10× formamide buffer (23.75 ml formamide, 12.5 mg bromophenol blue, 12.5 mg xylene cyanol FF, 1 ml 0.5 M EDTA (pH 8.0), and 0.25 ml sterile water). The samples were loaded on an 8% polyacrylamine-8 M urea-TBE gel to fractionate the radiolabeled primer extension products. The gel was then dried and exposed on an X-ray film for autoradiography.

The level of COX2 transcript was measured by primer extension experiments in the control haploid strains (ρ+, ρ0, or synthetic ρ−) and in diploid cells derived from mating the ρ− cells to the strains containing the mouse TFB2M gene inserted into either the COX4 or the MTF1 gene. A similar experiment was performed in which the level of the HSP transcript was measured in the same RNA samples (i.e., the COX2 assay was repeated on two samples). These results demonstrated that mouse mitochondrial promoters are not functional in yeast, and that a single mouse mitochondrial transcription protein is not sufficient to activate mouse mitochondrial promoters.

Extension products of the size predicted for HSP transcription initiation were detected when all three mouse mitochondrial transcription genes were present in the strain, whereas no HSP extension products were detected in control reactions using RNA isolated from a similar strain containing only two of the mouse transcription genes. The shorter HSP extension products may result from RNA processing in the yeast mitochondria, alternative transcription start sites, secondary structure in the mouse tRNAphe sequence that leads to premature termination of the reverse transcriptase extension product, or any combination thereof.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A transmitochondrial eukaryotic cell having endogenous mitochondria from which endogenous mtDNA has been removed and replaced with an exogeneous mitochondrial genome, said exogeneous mitochondrial genome comprising an isolated mtDNA genome which, in said endogenous mitochondria, is viable and can replicate in said cell, wherein said eukaryotic cell is a yeast cell and said isolated mtDNA genome is an isolated animal mitochondrial genome.

2. The transmitochondrial cell of claim 1, further comprising an exogenous nuclear gene, wherein the exogenous nuclear gene is of the same species as the mitochondrial genome.

3. The transmitochondrial cell of claim 2, wherein said exogenous nuclear gene encodes a polypeptide involved in mitochondrial fusion.

4. The transmitochondrial cell of claim 3, wherein said exogenous nuclear gene encodes a polypeptide involved in replication of the mitochondrial genome.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial  Sequence
<220> FEATURE:
<223> OTHER INFORMATION: Oligonucleotide

<400> SEQUENCE: 1
acccaacgcg gcaaactaac c                                           21

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
tcttgttcgt ctgccaggct                                             20

<210> SEQ ID NO 3
<211> LENGTH: 41
<212> TYPE: DNA
<213> ORGANISM: Artificial Sequence
<220> FEATURE:
<223> OTHER INFORMATION: Oligonucleotide

<400> SEQUENCE: 3
ctgtctctta tacacatctg tcgacagaag ccactggagc a                     41

<210> SEQ ID NO 4
```

```
<211> LENGTH: 43
<212> TYPE: DNA
<213> ORGANISM: Artificial Sequence
<220> FEATURE:
<223> OTHER INFORMATION: Oligonucleotide

<400> SEQUENCE: 4
ctgtctctta tacacatctc ccgggctaat tctgtcagcc gtt            43

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide

<400> SEQUENCE: 5
gtacctataa ccagaccgtt cagc                                 24

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
cagcggcatc agcaccttgt c                                    21

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
gcagccacca ataaagaaag                                      20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
ggaccctcgt ttagccgttc                                      20

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
aggtggatta tttatagtgt gattattgcc                           30

<210> SEQ ID NO 10
<211> LENGTH: 34
<212> TYPE: DNA
<213> ORGANISM: Artificial Sequence
<220> FEATURE:
<223> OTHER INFORMATION: Oligonucleotide

<400> SEQUENCE: 10
```

```
ggagatcttg atgtatgagg ttgatgatgt tgga                            34

<210> SEQ ID NO 11
<211> LENGTH: 20
<212> TYPE: DNA
<213> ORGANISM: artificial sequence
<220> FEATURE:
<223> OTHER INFORMATION: oligonucleotide

<400> SEQUENCE: 11
cccgcaaaca aagatcaccc                                            20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
atcatgtaat tctaaaatac                                            20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
tcatgcttgt tagacataaa                                            20

<210> SEQ ID NO 14
<211> LENGTH: 19
<212> TYPE: DNA
<213> ORGANISM: Artificial Sequence
<220> FEATURE:
<223> OTHER INFORMATION: oligonucleotide

<400> SEQUENCE: 14
cctatagtga gtcgtatta                                             19
```